United States Patent
Douglas et al.

(10) Patent No.: US 8,011,365 B2
(45) Date of Patent: Sep. 6, 2011

(54) MECHANICAL VENTILATION IN THE PRESENCE OF SLEEP DISORDERED BREATHING

(75) Inventors: Robert Douglas, Newport (AU); Anthony John Ujhazy, East Lindfield (AU); Glenn Richards, Clevedon (NZ); Mark David Buckley, Buchendorf (DE); Klaus Henry Schindhelm, Glenhaven (AU)

(73) Assignee: Resmed Limited, New South Wales (AU)

( * ) Notice: Subject to any disclaimer, the term of this patent is extended or adjusted under 35 U.S.C. 154(b) by 1177 days.

(21) Appl. No.: 10/596,860

(22) PCT Filed: Dec. 24, 2004

(86) PCT No.: PCT/AU2004/001833
§ 371 (c)(1),
(2), (4) Date: Mar. 14, 2007

(87) PCT Pub. No.: WO2005/063323
PCT Pub. Date: Jul. 14, 2005

(65) Prior Publication Data
US 2007/0215146 A1 Sep. 20, 2007

Related U.S. Application Data

(60) Provisional application No. 60/533,411, filed on Dec. 29, 2003, provisional application No. 60/545,658, filed on Feb. 18, 2004.

(51) Int. Cl.
*F16K 31/02* (2006.01)
(52) U.S. Cl. .............................. 128/204.23; 128/204.21
(58) Field of Classification Search ............. 128/204.18, 128/204.21–204.23, 204.26
See application file for complete search history.

(56) References Cited

U.S. PATENT DOCUMENTS

| 5,551,419 A | 9/1996 | Froehlich et al. |
| 5,704,345 A * | 1/1998 | Berthon-Jones ......... 128/204.23 |
| 6,761,167 B1 | 7/2004 | Nadjafizadeh et al. |
| 2002/0088465 A1* | 7/2002 | Hill ........................... 128/204.23 |
| 2004/0112382 A1 | 6/2004 | Schneider et al. |

FOREIGN PATENT DOCUMENTS

| DE | 10164446 | 7/2003 |
| EP | 0188071 | 8/1988 |
| EP | 0956877 | 11/2003 |
| GB | 2294400 | 5/1996 |
| JP | 2001259036 | 9/2001 |
| JP | 2004105230 | 9/2003 |
| WO | 03/039637 | 5/2003 |
| WO | 2004/078246 | 9/2004 |

* cited by examiner

*Primary Examiner* — Kristen Matter
(74) *Attorney, Agent, or Firm* — Gottlieb Rackman & Reisman PC

(57) ABSTRACT

A method for controlling operation of a CPAP apparatus. The apparatus has a blower (2), a patient interface (6), an air delivery conduit (8) for delivering air from the blower (2) to the patient interface (6), a sensor (4p) for determining the pressure in the patient interface (6), and a control mechanism (15) that causes air to be delivered at a desired pressure to the patient interface (6) and that detects transitions between inhalation and exhalation of a respiratory cycle of a patient in order to synchronise the blower output with the patient's efforts. In one form the CPAP apparatus provides pressure in accordance with a bi-level waveform with at least one characterising parameter of the waveform being automatically adjusted in accordance with indications of sleep disordered breathing. The indications of sleep disordered breathing can be one or more of snoring, apnea, hypopnea, and flow limitation.

36 Claims, 10 Drawing Sheets

MECHANICAL VENTILATION IN THE PRESENCE OF SLEEP DISORDERED BREATHING

This application is a U.S. National Phase Application of PCT/AU2004/01833 filed Dec. 24, 2004 and claims priority to U.S. Provisional Application No. 60/533,411 filed Dec. 29, 2003 and U.S. Provisional Application No. 60/545,658 filed Feb. 18, 2004, all of which are incorporated by reference.

1. FIELD OF THE INVENTION

This invention relates to mechanical ventilation of sleep disordered breathing (SDB).

2. BACKGROUND OF THE INVENTION

A comprehensive background discussion of mechanical ventilation can be found in "Principles and Practice of Mechanical Ventilation" (1994) Edited by Martin J Tobin, published by McGraw-Hill Inc., ISBN 0-07-064943-7.

The use of nasal Continuous Positive Airway Pressure (CPAP) to treat Obstructive Sleep Apnea (OSA) was invented by Colin Sullivan, see U.S. Pat. No. 4,944,310. Generally, the treatment involves providing a supply of air or breathable gas from a blower to a patient via an air delivery conduit and a patient interface. While treatment is effective, some patients find it uncomfortable. Improving patient comfort and compliance is a continuing challenge.

One way to improve comfort is to provide a more comfortable patient interface. In this regard, the ResMed MIRAGE™ masks have provided significant improvement in comfort. See U.S. Pat. Nos. 6,112,746; 6,357,441; 6,581,602 and 6,634,358. A more recent development is the ResMed MIRAGE™ ACTIVA™ mask series. See International Patent Application WO 2001/97893.

In the early days of nasal CPAP systems for treating OSA, patients were first titrated in a clinical study to determine an optimal treatment pressure. Titration involves a patient sleeping overnight in a clinic and being tested with a mask and CPAP device. The treatment pressure provided by the CPAP device is adjusted until apneas are eliminated. The treatment pressure is usually in the range of 4-20 $cmH_2O$. A device would be set to that pressure and given to the patient to take home. A subsequent development was the automatically adjusting device that a patient could take home. The automatically adjusting device will raise and/or lower the treatment pressure based on indications of obstructive sleep apnea, such as snoring. Such devices are sometime generically referred to as Automatic Positive Airway Pressure (APAP) devices. See U.S. Pat. Nos. 5,245,995; 6,398,739; and 6,635,021.

Another type of nasal CPAP device provides a first pressure during inhalation (sometimes termed an IPAP) and a second, lower pressure during exhalation (sometimes termed and EPAP). Examples of these include the ResMed VPAP™ series, and the Respironics BiPAP series. Bilevel CPAP devices may be prescribed for patients who do not comply with single pressure CPAP devices. Some patients perceive that the lower pressure during exhalation is more comfortable, at least while they are awake. A difficulty with these devices is deciding how to set the IPAP and EPAP pressures. If the EPAP is too low it may be insufficient to prevent obstructions, hence some clinicians may set the EPAP pressure to the pressure titrated during the sleep study. In those patients, the IPAP pressure, and thus the average pressure will be higher that that required to eliminate apneas.

Another form of automatically adjusting CPAP device is the ResMed AUTOSET™ SPIRIT™ device. In this device, the CPAP pressure is automatically increased or decreased in accordance with indications of flow limitation, such as flow flattening, snore, apnea and hypopnea. See U.S. Pat. Nos. 5,704,345; 6,029,665; 6,138,675; and 6,363,933. An advantage of an automatically adjusting system is that over time the treatment pressure required may vary for a particular patient and a correctly functioning automatic system can obviate the need the patient to return for a subsequent sleep study. These patents also describe a method and apparatus for distinguishing between so-called "central" and obstructive apneas. The contents of all of the aforesaid patents are incorporated by cross-reference.

Another device for treating certain types of Sleep Disordered Breathing such as Cheyne-Stokes Respiration (CSR) is the ResMed AutoCS™ device. Among other things, this device provides a supply of air or breathable gas with a smooth comfortable waveform, sophisticated tracking of the patient's respiratory phase, and servo-control of patient ventilation. See U.S. Pat. Nos. 6,484,719; 6,532,957; and 6,575,163 (the "AutoVPAP" patents). See also U.S. Pat. No. 6,532,959. The contents of these patents are all incorporated by cross-reference.

Some OSA patients find treatment with the above devices uncomfortable and they become non-compliant with the therapy. Other patients such as cardiovascular patients with Congestive Heart Failure, patients with REM Hypoventilation, and patients with Respiratory Insufficiency could also benefit from a more comfortable and/or effective form of therapy.

3. SUMMARY OF THE INVENTION

In accordance with a first aspect of our invention, there is provided a mechanical ventilator with a bi-level waveform and an automatically adjusting mean pressure.

In accordance with another aspect of our invention, there is provided a mechanical ventilator that automatically adjusts End Expiratory Pressure in accordance with airway patency.

The invention also includes in one form a bi-level CPAP device with an automatically adjusting IPAP.

Another aspect of our invention is to provide a bilevel CPAP device which adjusts the EPAP in accordance with indications of apnea and the IPAP in accordance with indications of flow limitation.

In accordance with another aspect of the invention there is provided a method and apparatus for determining when mouth leak is occurring.

In accordance with another aspect of the invention there is provided a mechanical ventilator that automatically adjusts End Expiratory Pressure in accordance with leak.

In one form of our invention, the proportion into the overall respiratory cycle of the patient is continuously determined, the proportion into the overall respiratory cycle being used to scale the time-length of a pressure-time template, with the pressure delivered to the patient following the shape of the template but having a swing adapted to patient requirements.

Additional aspects of the invention are described in more detail herein.

4. BRIEF DESCRIPTION OF THE DRAWINGS

5. DETAILED DESCRIPTION

5.1 Hardware

A device in accordance with an embodiment of the invention comprises a blower and blower-controller. The blower can deliver a supply of air at positive pressure 2-40 cmH$_2$O, but generally in the range of 4-25 cmH$_2$O to a patient interface via an air delivery conduit. The device also includes a flow sensor to measure the flow of air along the conduit, and pressure sensors to measure the pressure of air at the blower outlet. In one form, the device alternatively includes an additional pressure sensor to detect the pressure in the patient interface.

Figure 1:
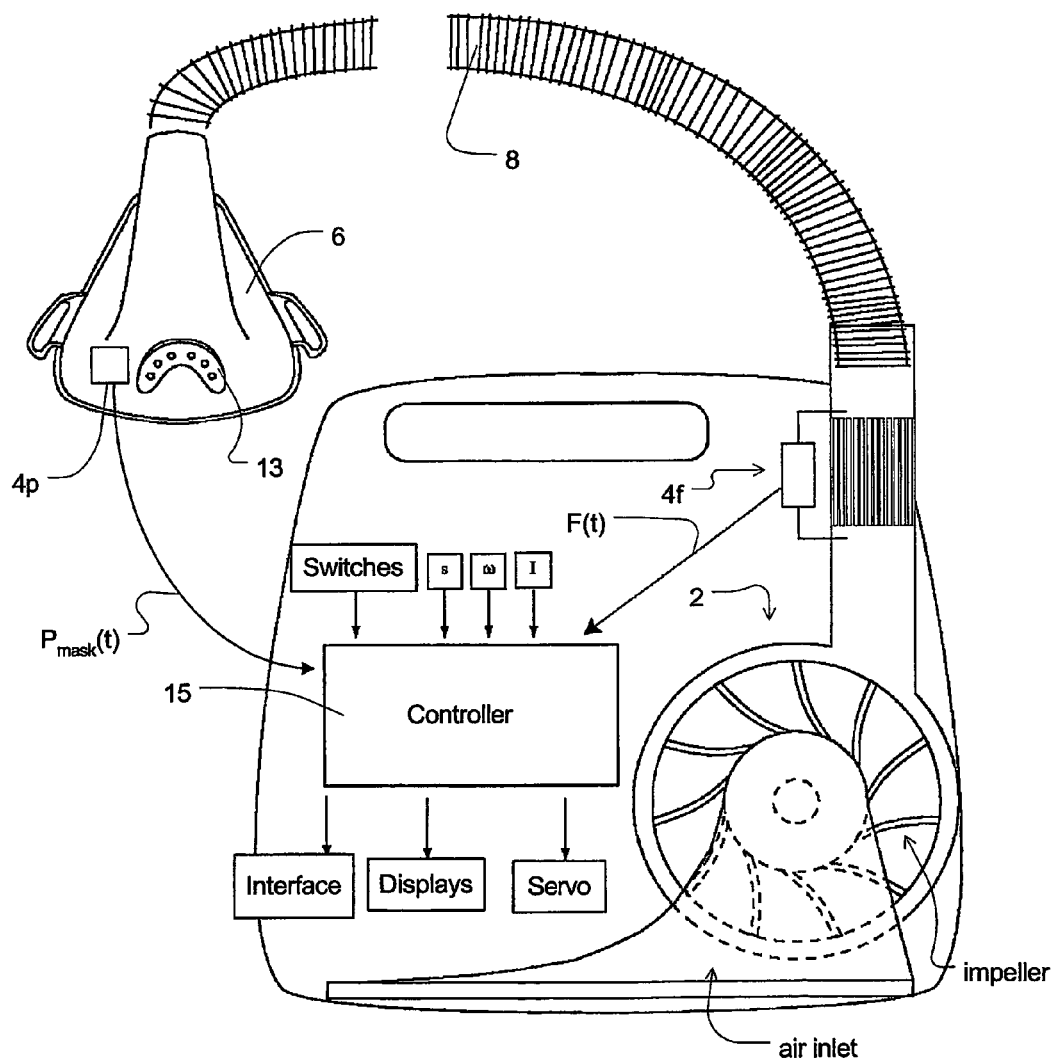
FIG. 1 depicts a structure of the preferred ventilator apparatus for implementing the methods of the current invention.

For example, a preferred embodiment of the invention is illustrated in FIG. 1. The ventilator device may include a servo-controlled blower 2, a flow sensor 4$f$, pressure sensor 4$p$, a mask 6, and an air delivery conduit 8 for connection between the blower 2 and the mask 6. Exhaust gas is vented via exhaust 13. Mask flow may be measured by a flow sensor, such as a pneumotachograph and differential pressure transducer to derive a flow signal F(t). Alternatively, the pneumotachograph may be replaced by a bundle of small tubes aligned in parallel with the flow from the blower with the pressure difference measured by the differential pressure transducer across the bundle. Mask pressure is preferably measured at a pressure tap using a pressure transducer to derive a pressure signal P$_{mask}$(t). The pressure sensor 4$p$ and flow sensor 4$f$ have been shown only symbolically in FIG. 1 since it is understood that those skilled in the art would understand how to measure flow and pressure. Flow F(t) and pressure P$_{mask}$(t) signals are sent to a controller or microprocessor 15 to derive a pressure request signal P$_{Request}$(t). The controller or processor is configured and adapted to perform the methodology described in more detail herein. The controller or processor may include integrated chips, a memory and/or other instruction or data storage medium to implement the control methodology. For example, programmed instructions with the control methodology are either coded on integrated chips in the memory of the device or loaded as software. As those skilled in the art will recognize, analog devices may also be implemented in the control apparatus. The apparatus of FIG. 1 includes other sensors, communication interfaces and displays, a servo, etc., functional blocks the details of which are not necessary for an understanding of the present invention.

5.2 Synchrony: Triggering, Cycling & Phase Determination

Figure 6:
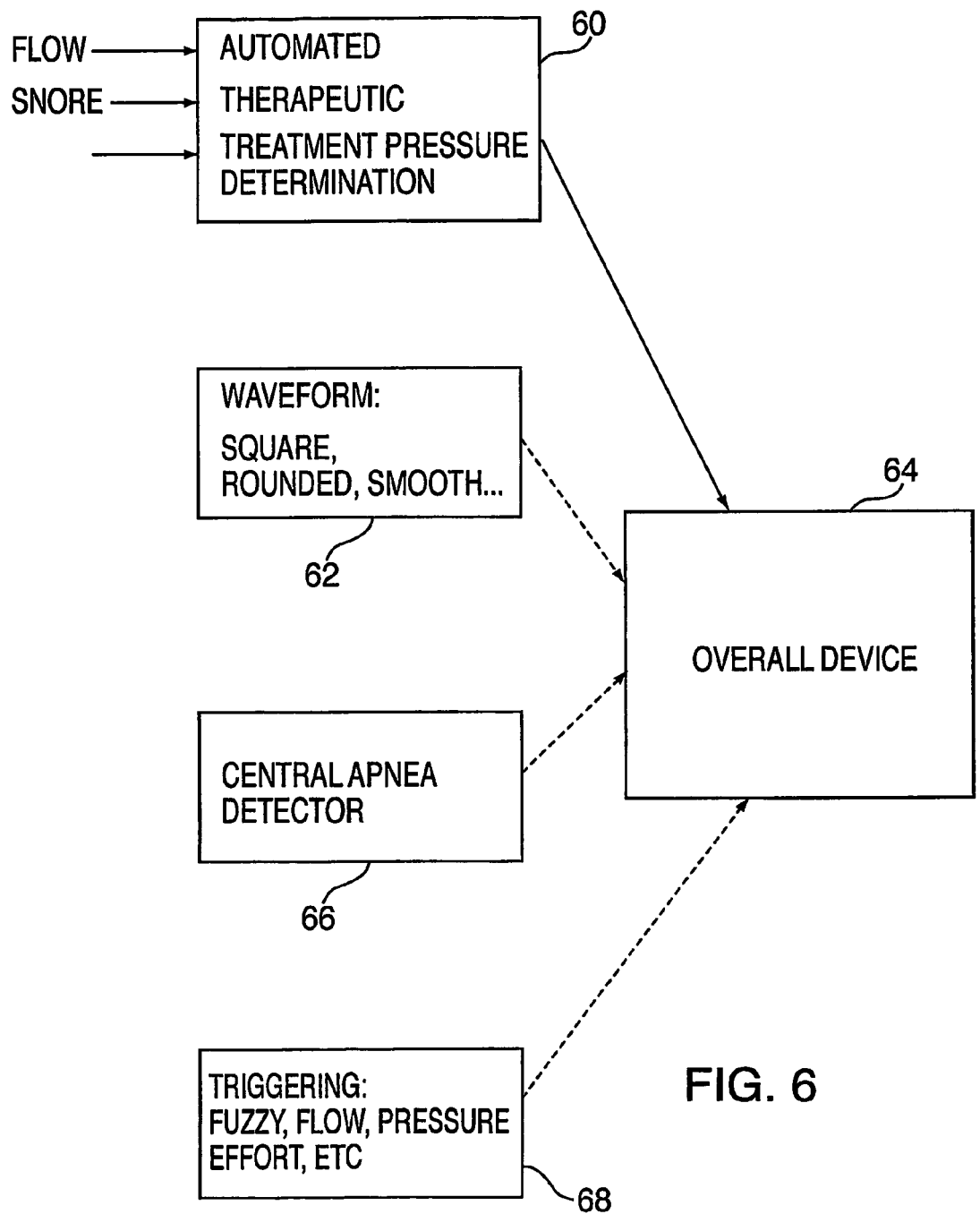
FIG. 6 is a block diagram of an embodiment of a device according to the invention.

In a device which varies treatment pressure throughout the respiratory cycle of the patient, it is more comfortable for the patient if the device varies the pressure in synchrony with patient efforts. As illustrated in FIG. 6, an overall device 64 constructed in accordance with the principles of our invention includes an automated therapeutic treatment pressure determination component module 60 which determines a treatment pressure component to treat SDB, and a waveform module 62 or process for setting or selecting a waveform (square, rounded, smooth, etc.) for modulating pressure in conjunction with the patient's respiratory cycle. Typically, the device will include a synchrony or triggering module 68 (controlled by fuzzy logic, pressure, patient effort, etc.) for determining states or the phase within the patient's respiratory cycle. Optionally, a central apnea detector 66 may be included.

In delivering pressure, the triggering module monitors the patient to make a determination of the patient's respiratory phase in order to synchronise the blower output with the patient's efforts. In one form, the determination is whether the patient is inhaling or exhaling (a discrete variable). In another form, the determination is of the proportion into the overall respiratory cycle of the patient (a periodic variable). Determination of phase may be made by some combination of pressure, flow and effort sensors. For example, in one form, when mask pressure drops below a threshold, the transition to inhalation is taken to have occurred and correspondingly when mask pressure rises above a threshold, the transition to exhalation is taken to have occurred. In another form, when patient respiratory flow exceeds a threshold, inhalation is taken to have started and when patient respiratory flow falls below a threshold, exhalation is taken to have started. In another form, patient respiratory phase is determined from analysing the shape of the respiratory flow curve and making a number of determinations as to the extent to which it is early inspiration, middle inspiration, late inspiration, early exhalation, mid-exhalation and late exhalation. See U.S. Pat. Nos. 6,484,719; 6,532,957; and 6,575,163. Once a determination of phase has been made, the shape of waveform to be delivered can be decided.

In one embodiment, a phase determination may be based on elapsed time of the particular portion of the cycle (inspiration or expiration) relative to a predicted total time for that particular portion of the cycle. For example, the phase within the respiratory cycle is determined as a ratio of the elapsed time to the expected total time. Since the total time for the current cycle is not yet known, it is predicted by using an average time taken from a number of previous breaths, preferably taken from the previous five breaths of the patient. In the preferred embodiment, irregular breaths are excluded from the average. Thus, breaths of less than 150 milliseconds indicative of a cough or hiccup are excluded. Those skilled in the art will understand how to determine such a five breath average from a flow signal.

Figure 3:
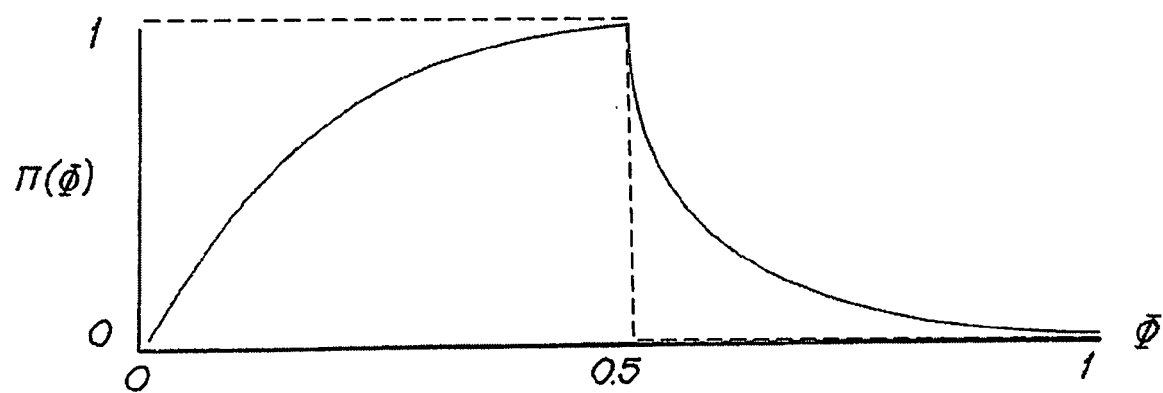
FIG. 3 is a pressure waveform template that is a function of a phase variable.
Figure 4:
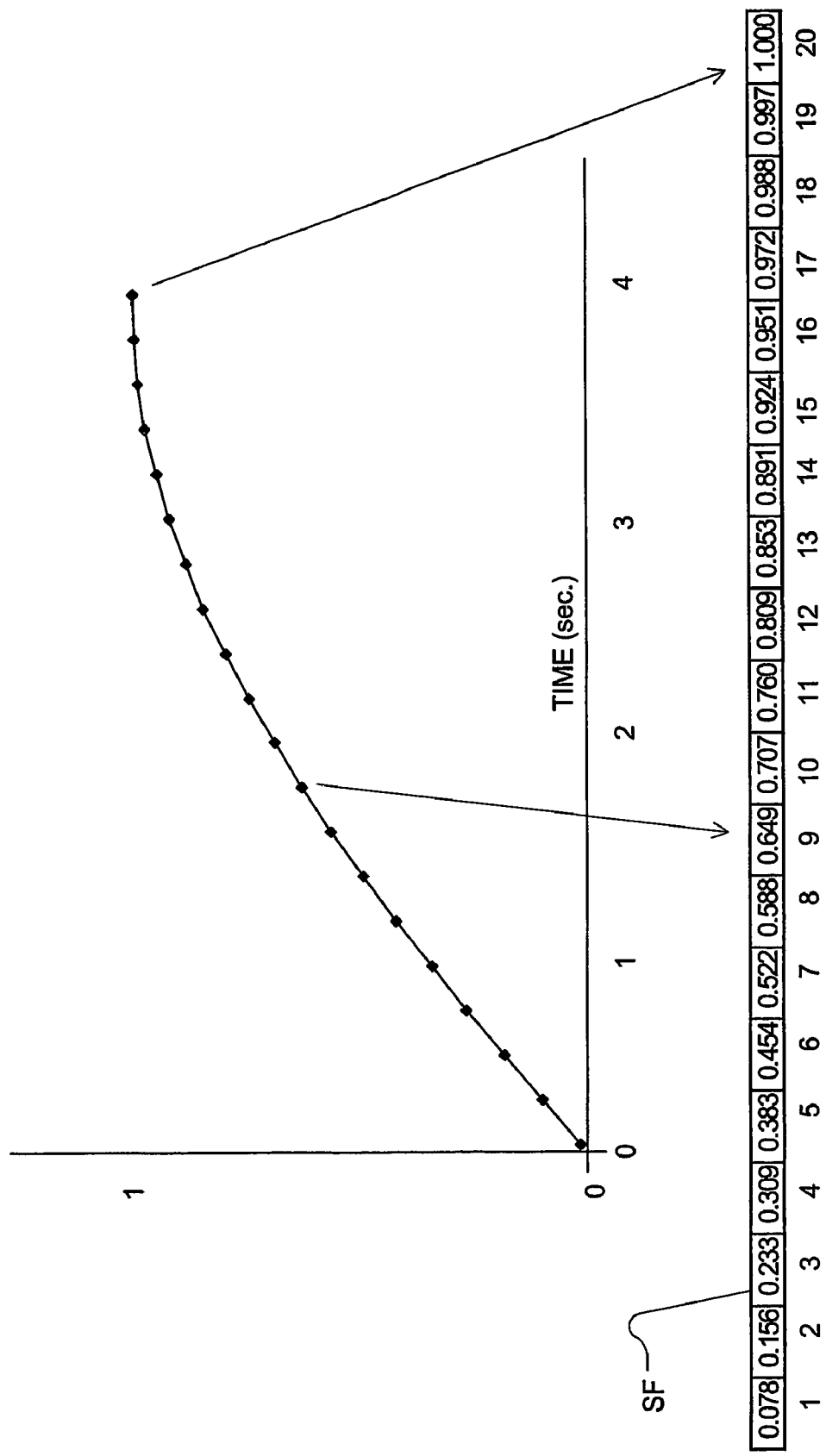
FIG. 4 is an inspiratory table of the inspiratory portion (0-0.5) of the waveform of the graph of FIG. 3.
Figure 5:
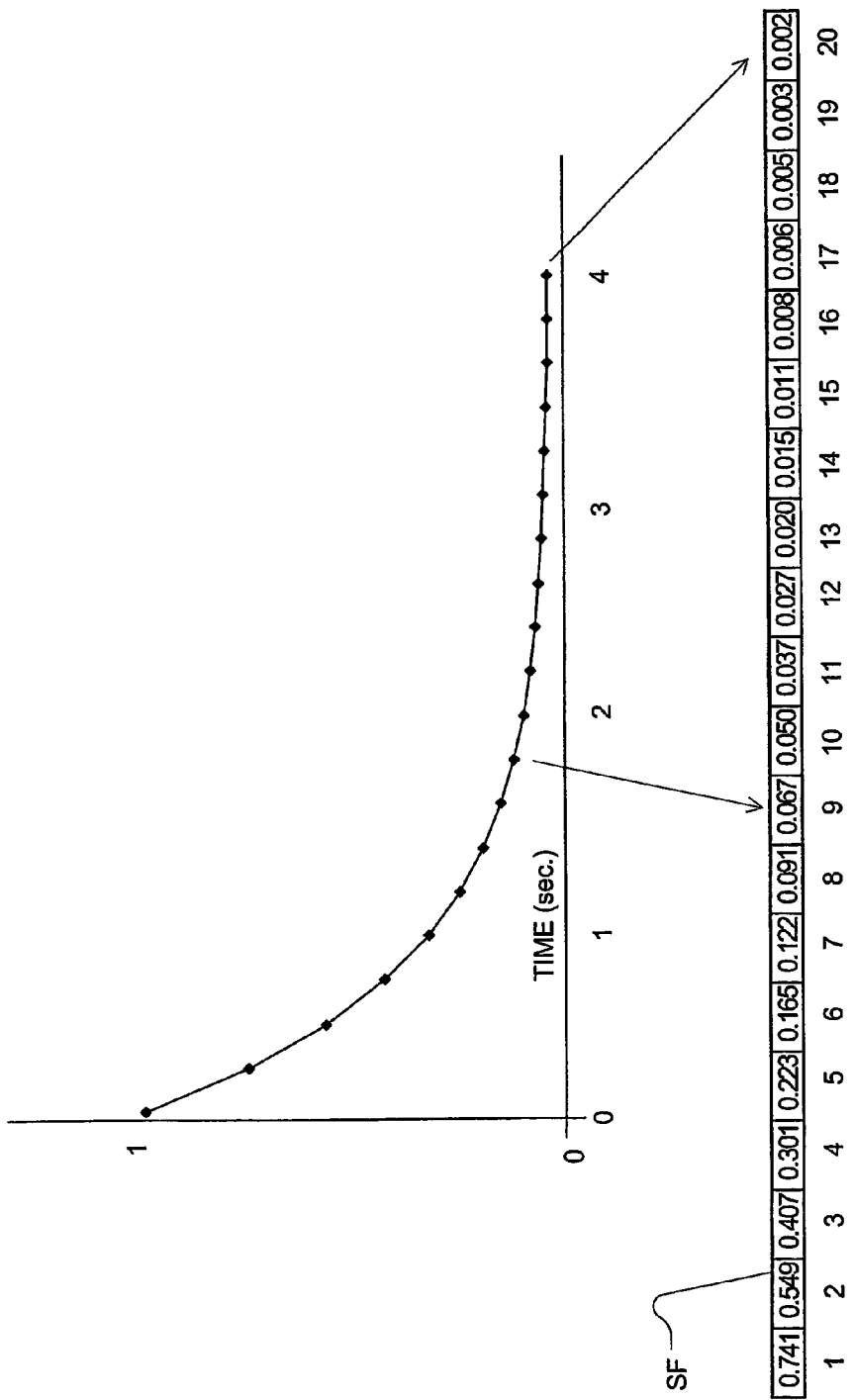
FIG. 5 is an expiratory table of the expiratory portion (0.5-1) of the waveform of the graph of FIG. 3.

With the determination of a continuous phase and utilizing the waveform module 62, smooth pressure changes are then implemented utilizing a pressure waveform template for inspiration and expiration that may preferably be stored in tables or arrays. In general, the tables store scaling factors for a predetermined breath length that when multiplied by a pressure amplitude in sequence will result in a pressure waveform that is represented by the scaling factors. Versions of these tables are illustrated in FIGS. 4 and 5 based on the smooth waveform of FIG. 3. As those skilled in the art will recognize, the tables may be substituted by mathematical equations rather than relying on a look-up operation. Moreover, although a sinusoidal rise/exponential decay curve is shown, the template may represent any shape of waveform, such as a square wave illustrated by the dashed lines of FIG. 3. Use of the phase variable ensures that each scaling factor (SF) of the table is utilized at an appropriate time in the patient's respiratory cycle, thereby compressing or expanding the time-length of the template. In this regard, the determined phase variable (elapsed time over total expected time) is used to scale the time-length of the template.

For these ends, a look-up operation that returns a pressure modulating function (Ins_Waveform) utilizing such a phase and an inspiratory table or array may be accomplished with the following:

Ins_Waveform=Inspiratory_Table($I$-Location)

where:

Inspiratory_Table is a function that returns a scaling factor from the table or array at a particular location determined by the I-Location function;

I-Location is a function that essentially identifies an inspiration phase variable within the current inspiration (i.e., the ratio of the elapsed inspiration time to the expected total inspiration time) of the patient as this relates to selecting an appropriate scaling factor from the table that will permit the delivered pressure to be modulated like that of a normal inspiration within the time scale of the patient's current predicted inspiration.

To accomplish this, the function returns an index of the inspiratory table as a function of (a) the current elapsed time of the inspiration (t_switch), (b) the time-length of the inspiratory portion of the waveform of the waveform template, which may be the number of table or array entries over which the inspiratory portion of the waveform template has been recorded in the table (total_entries); and (c) the predicted time for the inspiration portion of the respiratory cycle, i.e., the average inspiratory time (ave_insp_time). This index may be derived by the following formula:

index=round(t_switch*total_entries/ave_insp_time)

Similarly, the look-up operation (Exp_Waveform) on the expiratory table or array may be accomplished with the following functions:

Exp_Waveform=Expiratory_Table($E$-Location)

where:

Expiratory_Table is a function that returns a scaling factor from the expiration table or array at a particular location determined by the E-Location function;

Much like the I-location function described above, E-Location is a function that essentially identifies an expiration phase variable within the current expiration of the patient (i.e., the ratio of the elapsed expiration time to the expected total expiration time) for the purpose of selecting an appropriate scaling factor from the table that will permit the delivered pressure to be modulated like that of a normal expiration but within the time scale of the patient's current predicted expiration.

To accomplish this, the function identifies an index of the expiratory table as a function of (a) the current elapsed time of the expiration (t_switch), (b) the time-length of the expiratory portion of the waveform of the waveform template, which may be the number of table or array entries over which the expiratory portion of the waveform template has been recorded in the table (total_entries); and (c) the predicted time for the inspiration portion of the respiratory cycle, i.e., the average inspiratory time (ave_exp_time). The index may be derived by the following formula:

index=round(t_switch*total_entries/ave_exp_time)

Those skilled in the art will recognize that other formulas may be utilized for modulating the ventilation pressure, such as a more simple cycling and triggering between an IPAP and EPAP.

5.3 Indications of Sleep Disordered Breathing (SDB)

There are a number indications which can be used to detect sleep disordered breathing including snore, apnea, hypopnea and the shape of the inspiratory flow-time curve.

5.3.1 Snore

Snoring can be detected by a number of techniques as known in the art. For example, U.S. Pat. Nos. 5,245,995 (Sullivan et al.) and 5,704,345 (Berthon-Jones). For example a flow signal can be band-pass filtered in the frequency range of 30-300 Hz and the intensity of the resultant signal determined.

Having detected snoring, a snore index can be calculated as described in the above patents. The index can be based on the intensity, frequency and duration of snoring. A "snore prevention pressure" can be defined as the minimum CPAP pressure necessary to prevent snoring.

5.3.2 Apneas & Hypopneas

Apneas can be detected using a number of techniques as known in the art. For example, U.S. Pat. No. 5,704,345 (Berthon-Jones) describes an apnea detector as follows: The average flow signal variance calculated over a moving time window is compared with a threshold by a level detector, to generate an "airflow-ceased" trigger. This starts a timer. If the trigger persists for more than 10 seconds, a comparator declares an apnea. The threshold may be a fixed value, typically 0.1 l/sec, or may be a chosen percentage (typically 10 or 20%) of the average ventilation over the last several minutes (typically 5 minutes). For convenience, instead of comparing the threshold with the square root of the variance, one can square the threshold, and compare with the variance directly.

Conversely, if airflow resumes before 10 seconds lapses, the timer is reset and no apnea is declared.

In one form, upon detection of an apnea, the device increases pressure until the apnea stops, or a predefined threshold is reached. In this way the pressure does not exceed safe levels. The amount of the increase in pressure can vary upon the pressure at which an apnea has occurred and the duration of the apnea. See U.S. Pat. No. 6,367,474 (Berthon-Jones et al.)

Hypopneas can be similarly detected, however with a higher threshold, such as 50% of the average ventilation.

5.3.3 Flow Limitation

Flow limitation can be detected by a number of techniques as known in the art. For example see U.S. Pat. No. 5,704,345 (Berthon-Jones) which describes using various flattening indices such as based on the mid-portion of the inspiratory flow-time curve. Other flattening indices are known. See U.S. Pat. No. 6,814,073 (Wickham). A flow limitation prevention pressure can be defined as the minimum CPAP pressure necessary to prevent flow limitation. This pressure is not predetermined, but calculated continuously in conjunction with various flow flattening indices. Pressure is increased until the indices indicate that flattening has been eliminated. The pressure level at which the indices indicate that flattening is eliminated is taken to be the current "flow limitation prevention pressure". In one form of our invention, the current "flow limitation prevention pressure" is automatically decreased with time unless an indication of flow limitation is detected.

5.4 Waveform Shape

Accordingly, the blower can deliver a generally square-shaped waveform, similar to that provided by the ResMed VPAP™ Series or a more rounded waveform, similar to that provided by the ResMed AUTOSET CST™ product (see U.S. Pat. No. 6,532,959), for example, having a sinusoidal rise and exponential decay. Furthermore, the blower can adjust the shape of the waveform between square and more rounded to balance comfort and effectiveness (See U.S. Pat. No. 6,553, 992). In one form, for example, when delivering a generally square wave, the device provides a higher pressure during an inspiratory portion of the patient's respiratory cycle (IPAP) and a lower pressure during an expiratory portion of the patient's respiratory cycle (EPAP). In another form, for example, when delivering a more rounded waveform, a SWING and pressure setting are determined. The SWING is the difference between the highest and lowest pressures delivered to the patient. The pressure setting could be the base pressure in one form, or the peak pressure in another form.

5.5 Some Embodiments of Our Invention 5.5.1 First Embodiment: Automatic IPAP

In accordance with a first embodiment of the invention, a device is adapted to provide a generally square waveform having settings for IPAP and EPAP in a manner similar to ResMed's VPAP III device. The device has a clinician-settable pressure setting for the difference between IPAP and EPAP, ΔP (sometimes called Swing). The device monitors patient flow and determines a treatment pressure using the same algorithm as ResMed's AUTOSET SPIRIT device. See U.S. Pat. No. 5,704,345. Upon detection of the beginning of inspiration, as described above, the device provides a supply of air at the treatment pressure (IPAP=treatment pressure) and maintains that pressure throughout the inspiratory portion of the patients breathing cycle. Upon detection of the beginning of exhalation, the device decreases the supplied pressure to the treatment pressure less ΔP.

In this way the advantages of the automatically adjusting CPAP algorithm are brought to a bi-level CPAP device.

5.5.2 Second Embodiment: Automatic EPAP or EEP

A second embodiment of the invention is similar to the first embodiment, except that the End Expiratory Pressure (EEP) or the EPAP pressure is automatically adjusted, and the IPAP is a fixed delta pressure above the EPAP.

5.5.3 Third Embodiment: Automatic Mean Pressure

A third embodiment of the invention is similar to the first embodiment, except that the mean or median pressures are automatically adjusted, and there is a fixed delta pressure between IPAP and EPAP.

5.5.4 Fourth Embodiment: Automatic Swing Control

Figure 8A:
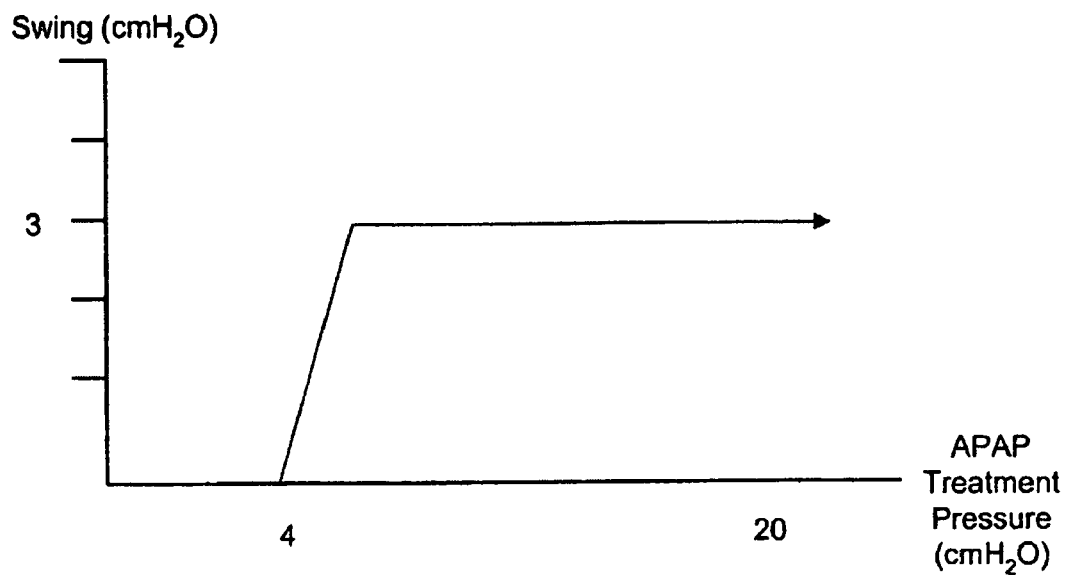
FIGS. 8A and 8B are illustrative functions for controlling swing as a function of an automatic SDB pressure determination process.
Figure 8B:
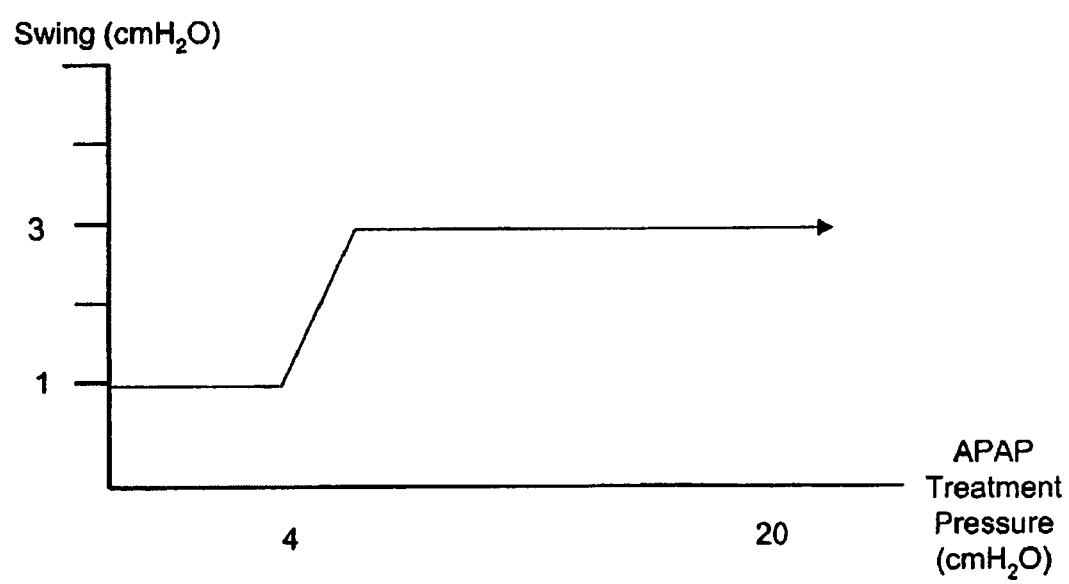
Figure 9:
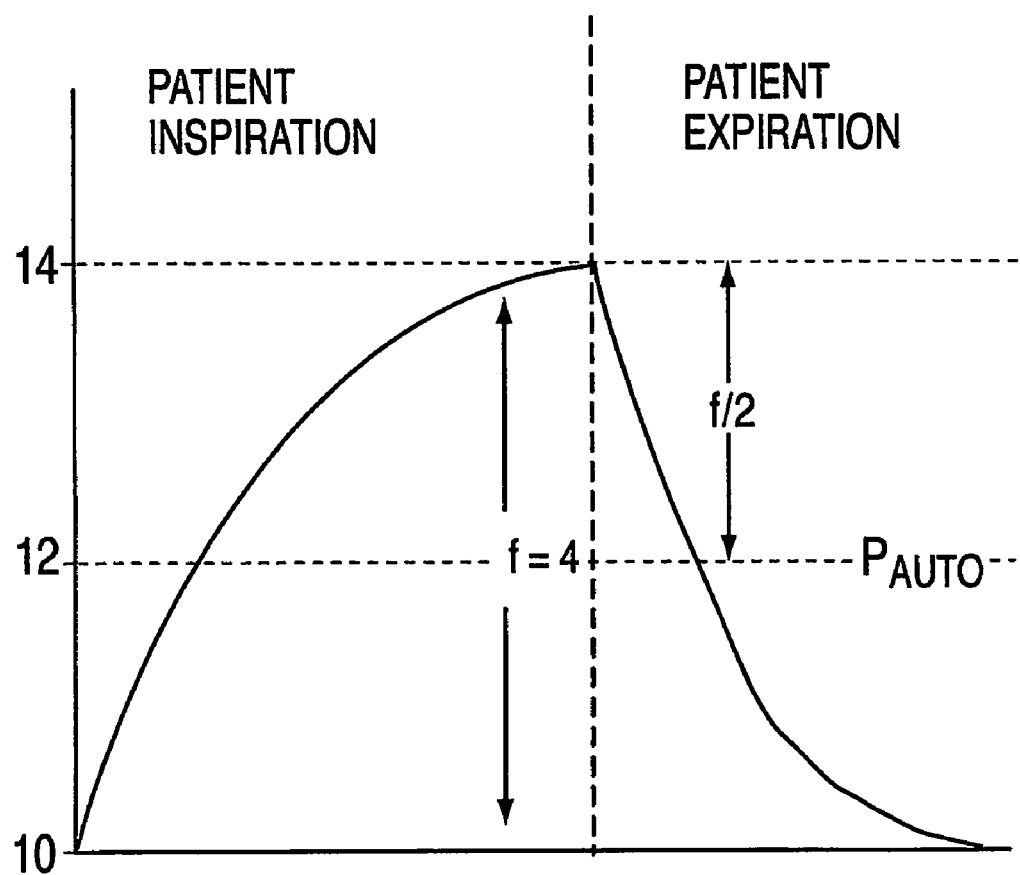
FIG. 9 is a graph illustrating control of median pressure by an automated SDB pressure detection process.

In accordance with another aspect of the invention, the therapeutic treatment pressure is used to control the pressure difference between IPAP and EPAP, or the "swing". For example, when the device determines that the treatment pressure is small, e.g., 5 cmH$_2$O, then the swing is set to a small value, e.g., 0 or 1 cmH$_2$O, and when the treatment pressure is large, e.g., 15 cmH$_2$O, the swing is set to a larger value, e.g., 3 or 4 cmH$_2$O. In this way a device in accordance with the invention can be controlled to ensure that pressure never drops below a threshold, for example, 4 or 5 cmH$_2$O. Such a form of control is illustrated by the function of FIG. 8A in which the swing is set as a function of detected therapeutic treatment pressure (APAP Treatment Pressure). An alternative function is illustrated in FIG. 8B in which the swing is restricted from falling below a minimum such as 1 cmH$_2$O.

Figure 7:
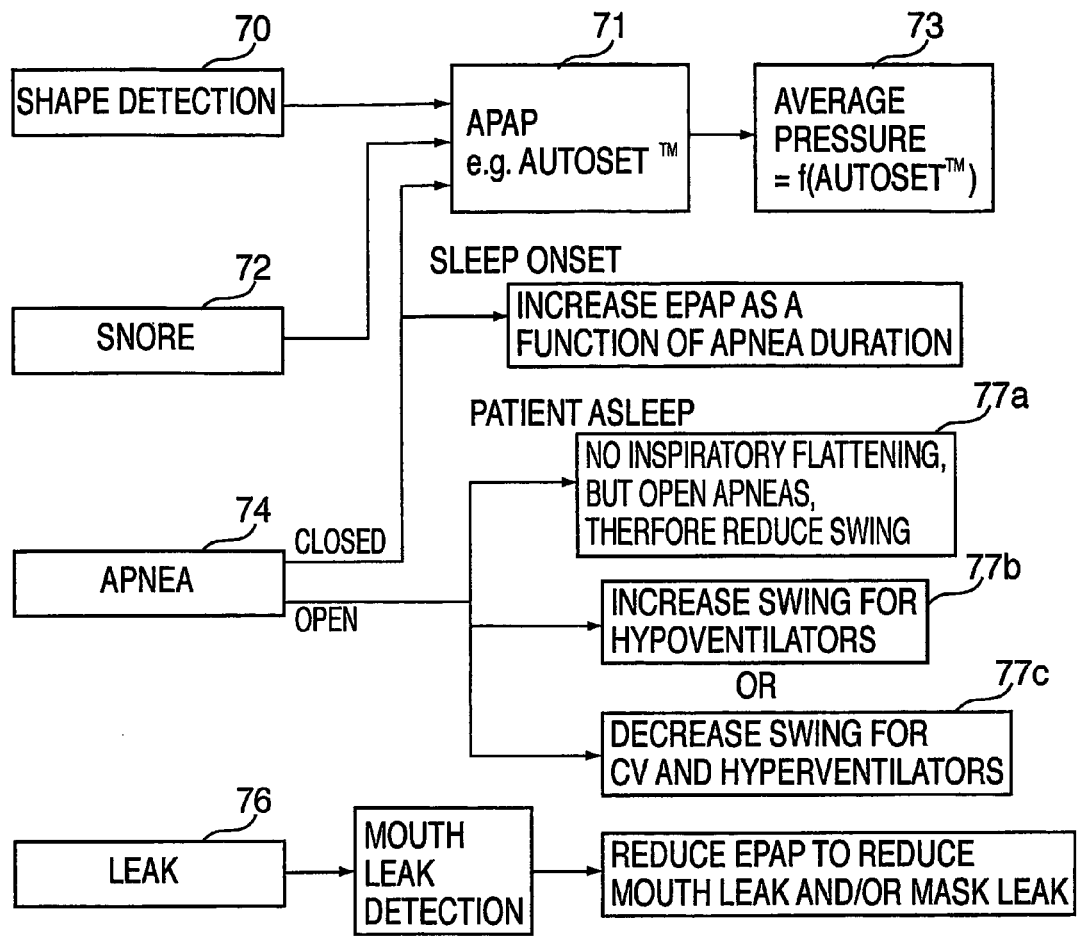
FIG. 7 is another block diagram illustrating an application of pressure to a ventilator of the invention.

As illustrated in FIG. 7, if an event of central apnea is detected, swing may be increased or decreased based on several conditions. For example, it may be reduced if partial obstruction is not detected. Alternatively, if based on an historic analysis of flow data performed by the device or a classification preset by a clinician, the current patient is a hypoventilator (has experienced hypoventilation), the swing may be increased, for example, by a step up in the swing by a predetermined amount. Alternatively, if based on an historic analysis of flow data performed by the device or a classification preset by a clinician the current patient is a hyperventilator or CV patient, the swing may be decreased, for example, by stepping down the swing by a predetermined amount.

5.5.5 Fifth Embodiment: "Shark-Fin" Waveform

A fifth embodiment of the invention is similar to embodiments one to three, except that instead of providing a generally square pressure-time waveform, the waveform has a "shark-fin" shape as indicated in FIGS. 2D, 3, 4 & 5.

5.5.6 Sixth Embodiment: Automatic IPAP and EPAP

In accordance with a sixth aspect of the invention, IPAP and EPAP are separately automatically adjusted. In this form of the invention, two pressure levels are calculated automatically. The first pressure is the minimum pressure necessary to prevent apneas and hypopneas. The second pressure is the minimum pressure necessary to prevent flow flattening. The EEP or EPAP is set to the first pressure and the IPAP is set to the second pressure.

The first pressure is calculated using the apnea and snore detectors described above. The second pressure is calculated from flow flattening or roundness indices as described above. The second pressure is controlled to be at least equal to the first pressure, preferably 1-2 cmH$_2$0 greater than the first pressure. In addition there is a predetermined maximum difference between the first and second pressures.

In one form, absent an indication of apnea or hypopnea the EPAP pressure is decreased. Similarly in one form, absent an indication of flow flattening the IPAP pressure is decreased.

5.5.7 Other Embodiments

The minimum pressure, P$_0$, delivered to the patient may be automatically controlled in conjunction with the pressure calculated by the automatic algorithms P$_{therapeutic}$ and an amplitude, A, calculated from the desired delta pressure between IPAP and EPAP. With regard to the preferred pressure delivery formula P(t) illustrated above, such implementations may be achieved by setting P$_0$ in alternative ways as follows:

$$P_0 = \begin{cases} P_{therapeutic} \\ P_{therapeutic} - A \\ P_{therapeutic} - \frac{A}{2} \\ P_{therapeutic} - kA \end{cases}$$

In the first, the therapeutic adjustments generated from the SDB detection routine discussed above are applied to the end expiratory or baseline pressure. In the second, therapeutic adjustments are applied to the peak or end inspiratory pressure. In the third, therapeutic pressure is applied to the mean. Those skilled in the art will recognize that each of the first three may be derived by the fourth formula by setting adjustment variable K appropriately. In one form, a waveform template function, such as one illustrated in FIG. 3 (either the solid smooth waveform or the dashed square wave), may be modified for purposes of applying the therapeutic adjustments to either the baseline, peak or median by adjusting the y-axis of the template to vary from either 0 to 1, −1 to 0, or −0.5 to 0.5 respectively. In such an embodiment, P$_0$ may be adjusted directly by the therapeutic pressure determination process.

Similarly, as illustrated in the flow chart of FIG. 7, an embodiment of a bi-level device having IPAP and EPAP, the apparatus may increase the EPAP pressure as a function of apnea duration determined in the apnea detector 74.

Figure 2A:
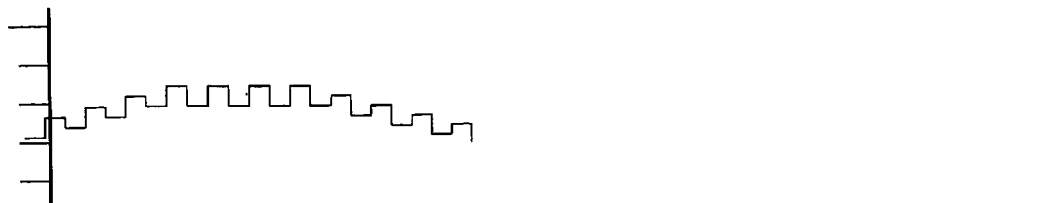
FIGS. 2A-2D illustrate some exemplary waveforms delivered according to various embodiments of the invention.

Several examples of resulting waveforms that may be generated by a device in accordance with various embodiments of the invention are illustrated in FIGS. 2A-2D. In FIG. 2A a square wave is generated based on a fixed swing. The average of the ventilation pressure modulation gradually rises and then falls over time as a result of the automated detection of a therapeutic pressure that may be applied to the baseline, peak or median as previously discussed.

Figure 2B:

In FIG. 2B, the therapeutic pressure is applied to the peak pressure or swing of a square wave while the baseline is held fixed resulting in a gradually increased and then decreased swing or peak. This may be accomplished by varying or controlling the peak and/or the swing as a function of the therapeutic pressure while maintaining the baseline pressure fixed.

Figure 2C:
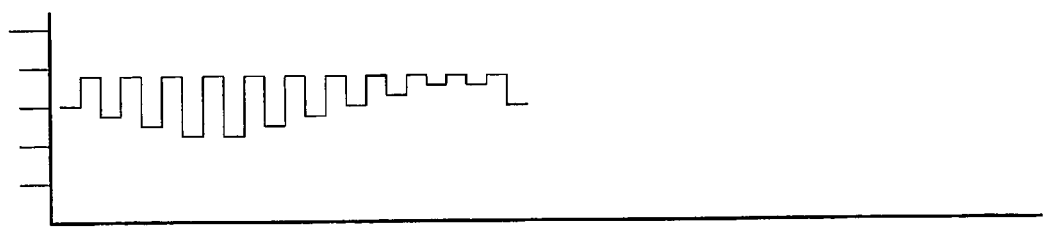

In FIG. 2C, the automatically detected therapeutic pressure is applied to the baseline pressure or the swing of a square wave. This may be accomplished by varying or controlling the baseline and/or the swing as a function of the therapeutic pressure while maintaining the peak pressure fixed.

Figure 2D:
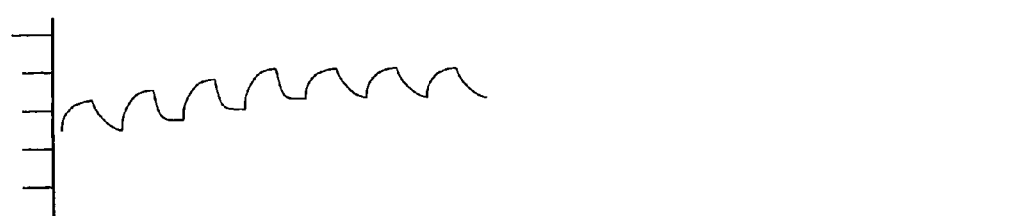

In FIG. 2D, the automatic control described above with regard to FIG. 2A is illustrated with a smoother waveform function. Those skilled in the art will recognize that the control described in FIGS. 2A to 2C can also be applied to the smooth waveform function illustrated in FIG. 2D with results similar to that of FIGS. 2A to 2C respectively.

5.6 Other Aspects 5.6.1 Mouth Leak Detection

Figure 10:
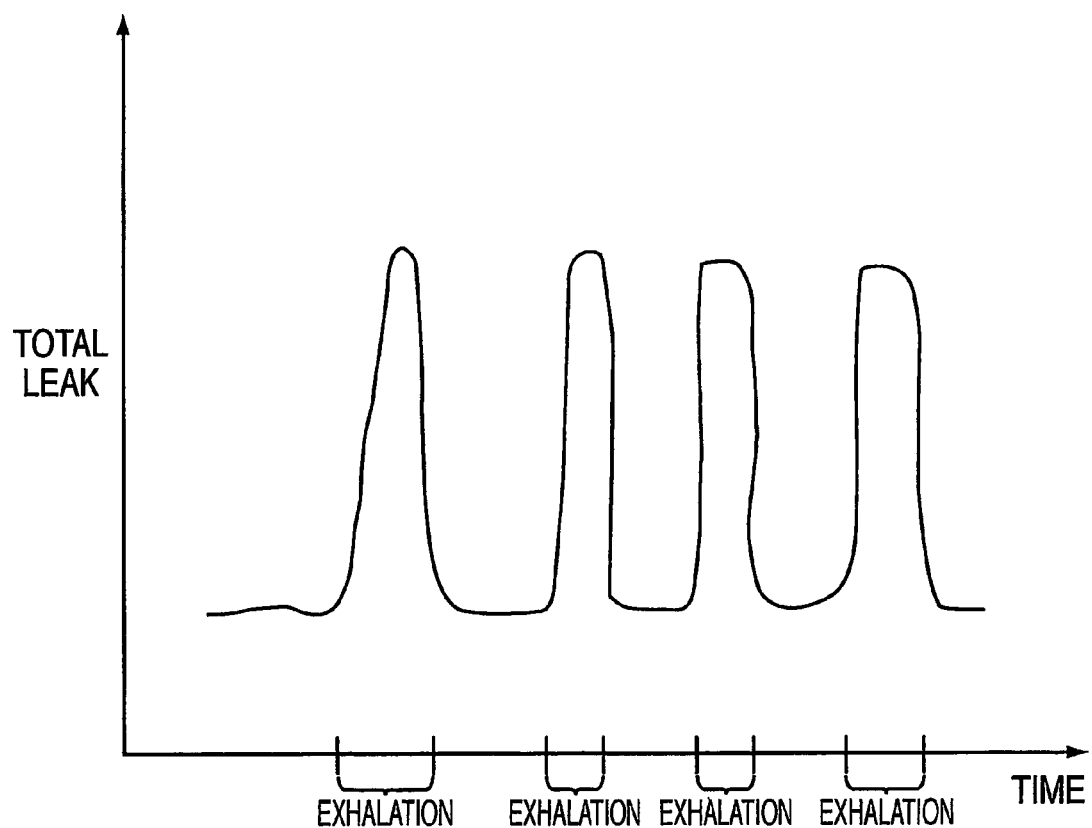
FIG. 10 is a graph illustrating mouth leak detection.

In one form, the apparatus includes mouth leak detection apparatus, particularly useful for detection of mouth leak when a nasal mask is used. During such treatment when a patient's mouth is open, typically occurring during exhalation, air delivered to the nasal mask may escape through the mouth, through the nose, and out the mouth if the mouth is opened. This is illustrated in the graph of FIG. 10. Thus, the apparatus may include a module, such as a software module or process, that receives a signal indicative of total leak from the mask, as well as a signal indicating whether the patient is inhaling or exhaling. Additionally or alternatively, the software module receives a signal which includes markers indicating trigger and cycle time points. The mouth leak detection software module analyzes the total leak signal and determines whether or not there is a mouth leak, or that the mouth has opened resulting when leak increases coincident with exhalation. Such openings or mouth leak determinations may be counted and with the advent of a certain number of such events, which may be recorded, an indicator or warning from the device may inform the user or patient that a full face mask should be used. Alternatively, as illustrated in FIG. 7, in the presence of leak, the EPAP pressure or end expiratory pressure may be reduced to reduce mouth leak or any other detected mask leak. In one form, the software module integrates the total leak flow during inhalation to calculate total inhalation leak volume. A similar calculation is made to determine total leak exhalation volume. If the leak exhalation volume is greater than the leak inhalation volume by a threshold value, then the software module determines that mouth leak is present or that the mouth is opening or open during exhalation. The following equations may be used:

$$LV_i = avg_{Xbreaths}\left(\int_{t=trigger}^{t=cycle} Leak\, dt\right)$$

$$LV_e = avg_{Xbreaths}\left(\int_{t=cycle}^{t=trigger} Leak\, dt\right)$$

if $LV_e \rangle LV_i + LV_{threshold}$ then mouth leak

Once leak flow has been detected, the result may be flagged by generating a warning such as an audible or visible alarm, or recording the event in a data log.

5.6.2 Advantages of Our Invention

The advantages of our invention are many. Many patients find the delivery of high levels of positive pressure uncomfortable, and this may disturb sleep quality. The positive pressure delivered by prior art devices can lead to mask leaks, mouth leaks, upper airway symptoms, air swallowing and difficulty exhaling. A principle of treatment is to deliver the minimal possible effective pressure. An APAP device is designed to deliver the minimal possible effective pressure, which may vary within a night and from night to night. Bilevel devices have been used to reduce pressure during exhalation. Apparatus in accordance with an embodiment of the invention combines the features of APAP with bi-level ventilation to reduce mean pressure and increase comfort.

A disadvantage of bi-level ventilators, such as BiPAP, for providing comfortable therapy in OSA is the rate of pressure change at the transition from exhalation to inhalation and from inhalation to exhalation. A device in accordance with an embodiment of the invention utilises a more gradual change in pressure delivery during a breath, and copies flow rates observed during normal quiet breathing.

5.6.3 Work of Breathing (WOB)

In patients with poor lung compliance, work of breathing is a significant contributor to energy expenditure. OSA coexists with reduced lung compliance in some disease states, notably congestive heart failure (CHF) where SDB is present in 50-65% of patients. In CHF, CPAP has been demonstrated to improve heart function through a variety of mechanisms. CPAP is poorly tolerated in this group. A device in accordance with an embodiment of the invention offers advantages of CPAP plus the ability to decrease WOB. The bi-level waveforms used by a device in accordance with an embodiment of the invention reduce muscle work required for ventilation. A device in accordance with an embodiment of the invention may be useful in reducing metabolic rate and hence demands on the left ventricle.

Central apneas are a feature of worsening congestive heart failure and may require a different Positive Airway Pressure (PAP) therapy, for example, that provided by the AUTOSET CS™ device discussed above. A device in accordance with an embodiment of the invention can monitor the frequency of central apneas and provide a warning to the patient or clinician that a different form of treatment is indicated.

Regular CPAP may be difficult to use in CHF due to increased intrathoracic pressure impeding venous return and reducing systolic blood pressure. The bi-level waveforms and peak mean pressures only when necessary used by a device in accordance with an embodiment of the invention will lead to a reduction in this side effect of PAP in CHF.

Non-Invasive ventilators are generally set a pressure that normalise ventilation throughout the night. In Rapid Eye Movement (REM) sleep, physiologic changes in respiratory drive, respiratory muscle tone and upper airway tone predispose to added reductions in ventilation compared to other sleep states. Ventilation required during other sleep states may be considerably less. In a device in accordance with an embodiment of the invention, the EPAP pressures are lower during non-REM sleep.

In some patients, particularly those with obesity hypoventilation and other causes of hypercapnic respiratory failure, the increased Upper Airway (UA) resistance encountered in REM is an important factor in observed reduction in ventilation. In a device in accordance with an embodiment of the invention, EEP is raised in response to airflow flattening in order to counter the effect which a changing UA resistance may have on ventilation. Thus, in a device in accordance with an embodiment of the invention, by using the minimum necessary EEP required to keep upper airway patency, mean pressures are reduced leading to increased comfort.

Compliance is an issue with low rates of acceptance of therapy with some conditions such as amyotrophic lateral sclerosis and obstructive airways disease. An important factor is expiratory pressure. A device in accordance with an embodiment of the invention provides for a gradual elevation in expiratory pressures, and lowest possible mean pressures during therapy.

Many prior art ventilators use non-physiologic waveforms. While a fast rise-time is important for some patients, for other patients it is more important to have a comfortable waveform. Hence a device in accordance with an embodiment of the invention provides a range of waveforms including more rounded, physiologic shaped waveforms with, for example, a slow falling pressure. The slow falling pressure can be particularly useful for Chronic Obstructive Pulmonary Disorder (COPD).

Although the invention has been described with reference to various embodiments as described above, it is to be understood that these embodiments are merely illustrative of the application of the various principles of the invention. Numerous modifications, in addition to the illustrative embodiments of the invention discussed herein, may be made and other arrangements may be devised without departing from the spirit and scope of the invention.

For example other automatic CPAP algorithms may be used to determine the treatment pressure, such as $P_{crit}$ (for example, as described in U.S. Pat. No. 5,645,053 (Remmers et al.).

We claim:

1. In a CPAP apparatus having (i) a blower, (ii) a patient interface, (iii) an air delivery conduit for delivering air from the blower to the patient interface, (iv) a sensor adapted to generate a first signal determined from pressure in the patient interface, (v) a sensor adapted to generate a second signal determined from flow of air to the patient, (vi) a synchrony module programmed to determine transitions between inspiration and expiration of the patient's breathing cycle from at least one of said sensors, and (vii) a control mechanism programmed to provide a supply of air from said blower to the patient interface at positive pressure in accordance with a pressure-time template, a method of controlling the blower operation comprising the steps of:

automatically determining from at least one of said first and second signals the presence of a first sleep disordered breathing event; said first sleep disordered breathing event being categorized as an apnea, a hypopnea, or a snore; and automatically determining from at least one of said first and second signals whether there is present a second sleep disordered breathing event; said second sleep disordered breathing event characterized by flow flattening, where said first and second events are determined from different characteristics of said first and second signals, automatically determining a first treatment pressure in accordance with the first sleep disordered breathing event and a second treatment pressure in accordance with the second sleep disordered breathing event, setting a pressure parameter of the pressure-time template to the first treatment pressure during the expiration phase of the patient's breathing cycle and setting a pressure parameter of the pressure-time template to the second treatment pressure during the inspiratory phase of the patient's breathing cycle, and controlling the blower to deliver a supply of air at positive pressure to the patient interface in accordance with the template and in synchrony with the patient's breathing cycles as determined by the synchrony module.

2. A method in accordance with claim 1 in which said template is one of a square wave and a shark-fin wave.

3. A method in accordance with claim 1 in which the first treatment pressure is an EPAP and the second treatment pressure is an IPAP.

4. A method in accordance with claim 1 in which the pressure-time template has a maximum allowable swing between the first treatment pressure and the second treatment pressure.

5. A method in accordance with claim 1 wherein the first treatment pressure is decreased in the absence of an indication of apnea, hypopnea and snoring.

6. A method in accordance with claim 1 wherein the second treatment pressure is decreased in the absence of an indication of flow flattening and snoring.

7. A method in accordance with claim 1 wherein said pressure-time template is stored in look-up tables or arrays.

8. An apparatus for treatment of sleep disordered breathing comprising:

a blower for providing to a patient a supply of air at a treatment pressure in phase with the patient's respiratory breathing cycle, the respiratory breathing cycle including an expiratory phase and an inspiratory phase;

a patient interface;

an air delivery conduit for delivering air from the blower to the patient interface;

a first sensor adapted to generate a first signal determined from the pressure in the patient interface;

a second sensor adapted to generate a second signal determined from the flow of air to the patient through the patient interface;

a synchrony module for detecting transitions between inspiration and expiration of the patient's breathing cycle from at least one of said sensors; and a controller programmed to:

(1) receive said first and second signals and in response thereto detect the presence of first and second sleep disordered breathing events, the first event being at least one of an apnea, a hypopnea, or a snore and the second event being a different flow limitation; and (2) set a first pressure as a function of the occurrence of the first event and set a second pressure as a function of the occurrence of the second event, the first pressure being used to determine the treatment pressure provided during the expiratory phase of the breathing cycle and the second pressure being used to determine the treatment pressure provided during the inspiratory phase of the breathing cycle.

9. The apparatus according to claim 8 wherein the second event is flow flattening.

10. The apparatus according to claim 8 wherein the first pressure is an EPAP or EEP pressure.

11. The apparatus according to claim 8 wherein the second pressure is an IPAP pressure.

12. The apparatus according to claim 8 wherein there is a predetermined maximum pressure difference between the first pressure and the second pressure.

13. The apparatus according to claim 8 wherein the controller is further programmed to provide the supply of air at positive pressure in accordance with a pressure-time template.

14. The apparatus according to claim 13 wherein the pressure-time template is a square wave.

15. The apparatus according to claim 13 wherein the pressure-time template is a shark-fin wave.

16. The apparatus according to claim 13 wherein the pressure-time template is stored in look-up tables or arrays.

17. The apparatus according to claim 8 wherein the controller is further programmed to decrease the first pressure in the absence of the detection of first events.

18. The apparatus according to claim 8 wherein the controller is further programmed to decrease the second pressure in the absence of the detection of second events.

19. In a CPAP apparatus having (i) a blower, (ii) a patient interface, (iii) an air delivery conduit for delivering air from the blower to the patient interface, (iv) at least one sensor adapted to sense pressure or flow and to generate at least one signal from said determined pressure or flow, and (v) a controller that determines transitions between inspiration and expiration of the patient's breathing cycle, and that causes said blower to provide a supply of air to the patient interface at positive pressure in accordance with a pressure-time template, a method of controlling the blower operation comprising the steps of:

determining the presence of a first sleep disordered breathing event from said at least one signal; said first sleep disordered breathing event being in the group consisting of an apnea, a hypopnea, or a snore; and the presence of a second sleep disordered breathing event from said at least one signal; said second sleep disordered breathing event being characterized by flow flattening; where said first and second events are determined from different characteristics of said at least one signal, setting a first pressure parameter of the pressure-time template for the expiration phase of the patient's breathing cycle in accordance with the first event and setting a second pressure parameter of the pressure-time template for the inspiratory phase of the patient's breathing cycle in accordance with the second event, and controlling the blower to deliver a supply of air at positive pressure to the patient interface in accordance with the template and in synchrony with the determined transitions between inspiration and expiration of the patient's breathing cycle.

20. A method in accordance with claim 19 in which said template is one of a square wave and a shark-fin wave.

21. A method in accordance with claim 19 in which the first pressure parameter is an EPAP and the second pressure parameter is an IPAP.

22. A method in accordance with claim 19 in which the pressure-time template has a maximum allowable swing between the minimum and maximum values of pressure that is delivered to the patient interface by the blower.

23. A method in accordance with claim 19 wherein the first pressure parameter is decreased in the absence of an indication of apnea, hypopnea and snoring.

24. A method in accordance with claim 19 wherein the second pressure parameter is decreased in the absence of an indication of flow flattening and snoring.

25. A method in accordance with claim 19 wherein said pressure-time template is stored in look-up tables or arrays.

26. An apparatus adapted for treatment of sleep disordered breathing comprising:

a blower for providing to a patient a supply of air at a treatment pressure in phase with the patient's respiratory breathing cycle, the respiratory breathing cycle including an expiratory phase and an inspiratory phase;

a patient interface, an air delivery conduit for delivering air from the blower to the patient interface, at least one sensor for sensing pressure in the patient interface or flow of air to the patient and to generate at least one signal determined from said sensed pressure or flow, and a controller for determining transitions between inspiration and expiration of the patient's breathing cycle;

determining the presence first and second sleep disordered breathing events based on sensed pressure or flow, the first and second events being different indications of sleep disordered breathing and being based on different characteristics of said at least one signal; said first event being at least one of an apnea, a hypopnea, or a snore and said second event being a flow limitation, and setting a first pressure as a function of the occurrence of one of said events and setting a second pressure as a function of the occurrence of the other of said events, the first pressure being used to determine the treatment pressure provided during the expiratory phase of the patient's breathing cycle and the second pressure being used to determine the treatment pressure provided during the inspiratory phase of the patient's breathing cycle.

27. The apparatus according to claim 26 wherein the second event is flow limitation.

28. The apparatus according to claim 26 wherein the first pressure is an EPAP or EEP pressure.

29. The apparatus according to claim 26 wherein the second pressure is an IPAP pressure.

30. The apparatus according to claim 26 wherein there is a predetermined maximum pressure difference between the first pressure and the second pressure.

31. The apparatus according to claim 26 wherein the controller causes the blower to provide the supply of air at positive pressure in accordance with a pressure-time template.

32. The apparatus according to claim 31 wherein the pressure-time template is a square wave.

33. The apparatus according to claim 31 wherein the pressure-time template is a shark-fin wave.

34. The apparatus according to claim 31 wherein the pressure-time template is stored in look-up tables or arrays.

35. The apparatus according to claim 26 wherein the controller further causes the blower to decrease the first pressure in the absence of the detection of first events.

36. The apparatus according to claim 26 wherein the controller further causes the blower to decrease the second pressure in the absence of the detection of second events.

* * * * *